United States Patent [19]

Hirai et al.

[11] Patent Number: 5,955,327
[45] Date of Patent: Sep. 21, 1999

[54] PROCESS FOR MANUFACTURING VEGETABLE LYSOLECITHINS

[75] Inventors: Hiroyuki Hirai, Ichishi-gun; Ryoji Sono, Matsusaka; Hen-Sik Koh, Ootsu, all of Japan

[73] Assignee: Tsuji Oil Mill Co., Ltd., Ichishi-gun, Japan

[21] Appl. No.: 09/056,869

[22] Filed: Apr. 8, 1998

[30] Foreign Application Priority Data

Apr. 8, 1997 [JP] Japan .................................. 9-089499

[51] Int. Cl.$^6$ ............................. C12P 13/00; C12P 7/64; C07F 9/10
[52] U.S. Cl. .......................... 435/128; 435/134; 435/198
[58] Field of Search ................................ 435/134, 128, 435/198

[56] References Cited

U.S. PATENT DOCUMENTS

| | | | |
|---|---|---|---|
| 4,220,551 | 4/1980 | Orthoefer | 554/80 |
| 4,221,731 | 9/1980 | Short et al. | 554/14 |
| 4,399,224 | 8/1983 | Flider et al. | 435/271 |
| 5,160,759 | 11/1992 | Nomura et al. | 426/602 |
| 5,716,814 | 2/1998 | Yesair | 435/134 |

OTHER PUBLICATIONS

APS Computer Abstract Yoshitomi et al JP 63–302929 "Production of Emulsifier Composition", Dec. 9,1988.
APS Computer Abstract EGI et al JP 62–279832 "Manufacture of Emulsifying Agent", Dec. 4, 1987.

*Primary Examiner*—Herbert J. Lilling
*Attorney, Agent, or Firm*—Jacobson, Price, Holman & Stern, PLLC

[57] ABSTRACT

In accordance with the present invention, there is provided a process for manufacturing vegetable lysolecithins which comprises allowing a hydrolysis enzyme consisting of phospholipase $A_1$ or $A_2$ to act on a hydrated lecithin used as a starting material, then adding for stirring to the resultant lysolecithin solution acetone in a proportion on a volume basis of either 1 to 4, or 5 or more, against the water contained in said resultant lysolecithin solution to thereby either float or precipitate the lysolecithin phase, then separating out said lysolecithin phase, followed by repetition of the acetone extraction procedure to separate for removal free fatty acids by-produced in the said lysolecithin production reaction as well as oil-soluble impurities originated from the starting material.

The process of the present invention can produce high-quality vegetable lysolecithins with reduced discoloration and improved flavor in increased yields.

8 Claims, No Drawings

PROCESS FOR MANUFACTURING VEGETABLE LYSOLECITHINS

The present invention relates to a process for manufacturing vegetable lysolecithins, and particularly to a process which permits high-quality vegetable lysolecithins with reduced discoloration and improved flavor to be produced in increased yields.

BACKGROUND OF THE INVENTION

Among lysolecithins of a plant origin, the soybean lysolecithin is understood to mean a 2-monoacylglycerophospholipid or 1-monoacylglycerophospholipid being produced through modification by allowing phospholipase $A_1$ or $A_2$ as a hydrolysis enzyme to act on water-treated soybean lecithin (1,2-diacylglycerophospholipid) to partially hydrolyze the fatty acid ester moieties of such phospholipid. As compared with normal soybean lecithin, such soybean lysolecithin can offer the characteristic features, such as (1) enhanced o/w emulsifying property, (2) increased emulsion stability retained under acid conditions and in the coexistence of salts, (3) improved effects developed in capability to bind to proteins and starches, and (4) excellent mold-releasing or pan-releasing property, and consequently, the demand for soybean lysolecithin is growing in recent years.

Soybean lecithin, which is used as a starting material for such soybean lysolecithin, is ordinarily produced in the form of paste-formed lecithin being composed of 60 to 65 weight % of phospholipid, 35 to 40 weight % of neutral oil and slight amounts of free fatty acids and sterols by filtering raw soybean oil, adding for stirring 2 to 3 weight % of water to soybean oil as warmed at 60 to 80° C., and subjecting a settled precipitate of a hydrated gum-like material (hydrated lecithin) to a degumming step of conducting separation by centrifugation, followed by heating for drying of the separated hydrated gum-like material under reduced pressure. And soybean lysolecithin is normally produced by adding water to such soybean lecithin (paste-formed lecithin) again, allowing phospholipase $A_1$ or $A_2$ to act on the mixture to hydrolyze the desired fatty acid ester moiety of each phospholipid under warming, heating the reaction mixture after conclusion of the reaction to thereby deactivate the enzyme, and then conducting heating and drying under reduced pressure, followed by filtration to remove the enzyme.

According as the demand for lysolecithins of a plant origin represented by such soybean lysolecithin has been increasing, however, the color phase, flavor and smell of the conventional lysolecithins are posing problems, being regarded as a matter of concern to the consumers. In order to alleviate or solve such problems, there has been developed the defatted lysolecithin which is manufactured by defatting a conventional lysolecithin by means of the extraction procedure with acetone to remove free fatty acids liberated during the enzymatic reaction and neutral oil, sterols, etc. derived from the starting material, with the result that the demand for the same is rapidly growing, but even such defatted product fails to solve the above-mentioned problems satisfactorily.

Thus, the discoloration and flavor deterioration of lysolecithin are in the first place brought about by heating the starting-material lecithin in the heating/drying step as described previously. In summary, lecithin, which is not heat-resistant and is easily susceptible to discoloration upon heating, is inevitably accompanied with discoloration in the concentration and drying step for the hydrated gum-like material, and tends to exhibit deteriorated flavor as well. Lysolecithin likewise is least heat-resistant, while on the other hand it has to be subjected to the enzyme deactivation step and also the second heating/drying step, and consequently, its discoloration and flavor deterioration inevitably constitute the problems being left unsolved. As a counter-measure for such defects, it may be conceivable to suppress the discoloration and flavor deterioration of lysolecithin by increasing the degree of depressurization in the drying step to thereby allow water evaporation at lowered temperatures. However this has been proven to produce the desired effect only to a limited extent, while it requires the filtration step to remove the enzyme, making the manufacturing process more complicated.

SUMMARY OF THE INVENTION

By taking such situations into consideration, the present invention has been completed, aid the problem that the instant invention is intended to solve lies in providing a process for producing high-quality vegetable lysolecithin with suppressed discoloration and improved flavor in increased yields.

In order to solve the said problem, the subject matter of this invention consists of a process for manufacturing vegetable lysolecithins from hydrated lecithin used as a starting material, which comprises allowing a hydrolysis enzyme consisting of phospholipase $A_1$ or $A_2$ to act on the hydrated lecithin to produce lysolecithin, then adding under stirring to the resultant lysolecithin solution acetone in a proportion on a volume basis of either 1 to 4, or 5 or more, against the water contained in said resultant lysolecithin solution to thereby either float or precipitate the lysolecithin phase, then separating out said lysolecithin phase, followed by repetition of the acetone extraction procedure to produce a vegetable lysolecithin with a high degree of purity in improved yields by separating for removal free fatty acids by-produced in the said lysolecithin production reaction as well as oil-soluble impurities originated from the starting material.

As is described in the above, the operational procedure of the present invention can offer the major characteristic feature in that a hydrated lecithin is subjected to enzymatic hydrolysis with a specific enzyme added, followed by direct acetone treatment of the resultant hydrolysate solution (an aqueous solution containing a mixture of phospholipids inclusive of the produced lysolecithins); namely, the above specified volume of acetone is added to allow lysolecithin to accumulate in the surface layer or bottom layer, followed by separation of the accumulated lysolecithin from the aqueous phase to thereby isolate the lysolecithin phase, whereby a loss of lysolecithin is minimized by avoiding wasteful disposal of lysolecithin in conjunction with the aqueous phase. In light of the fact that lysolecithin becomes by far more hydrophilic than lecithin, it was originally anticipated that acetone extraction treatment of an aqueous solution containing lysolecithin would not be effective in contrast to the case of lecithin as mentioned in the Official Gazette of Japanese Patent Publication No. Hei 5-43710, but the present inventors dared to conduct intensive investigation, leading to the finding that lysolecithin can unexpectedly be isolated effectively, although the formulated volume of acetone against the water content is slightly different from those in the case of lecithin.

As compared with the conventional processes, accordingly, the operational procedure of the present invention does neither lower the production yield of lysolecithin nor bring about increases in production costs, and also can eliminate entirely the twice repeated heating/concentration steps in the conventional processes or reduce either one of the steps, while it does not require either the heating deactivation step for removal of the enzymes or the filtration step necessitating warming for reduction of the viscosity, thus enabling discoloration, foul smelling and taste and flavor deterioration to be suppressed to the greatest extent and permitting high-quality lysolecithin to be produced in increased yields.

As a hydrated lecithin in the above operational procedure of the present invention, there can advantageously be used hydrated gum-like material generated in the degumming step for vegetable oils, which in turn offers the advantage that the twice repeated heating/concentration step as adopted in the conventional processes can be avoided, and in addition, it may be possible to utilize as a hydrated lecithin the ordinary, commercially available lecithin, or in other words paste-like lecithin obtained by heating and concentrating such hydrated gum-like material, but after being admixed with water. Even when such paste-like lecithin after being admixed with water is used as a hydrated lecithin, the heating/concentration step used in the conventional processes can be eliminated, and this enables the heating/concentration step after enzymatic hydrolysis to be eliminated at least once, thereby permitting discoloration and flavor deterioration to be suppressed in the resultant lysolecithin.

In the process for manufacturing vegetable lysolecithins according to the present invention, and after adding a specified enzyme to the hydrated lecithin to produce lysolecithin, no inconvenience could be brought about in subjecting the resultant lysolecithin solution to a deactivation treatment in order to prevent the enzymatic reaction from proceeding, prior to the procedure of separating the lysolecithin phase through the above-mentioned formulation of acetone, but in particular because the present invention can achieve effective enzyme removal by way of acetone treatment, the lysolecithin solution obtained by enzymatic hydrolysis of the hydrated lecithin can advantageously be subjected as such to the procedure of separating the lysolecithin phase through the formulation of acetone, without being subjected to such deactivation treatment, and this can advantageously eliminate the step of enzyme deactivation by heating at increased temperatures, thus permitting discoloration and flavor deterioration of the resultant lysolecithin to be alleviated more effectively.

In one desired embodiment of the present invention, there can be adopted another operational procedure which involves subjecting the resultant lysolecithin product obtained through the above-mentioned repeated extraction with acetone to a extraction treatment with a non-polar organic solvent. Such extraction treatment with a non-polar organic solvent, which can separate out effectively impurities in the lysolecithin product, makes it possible to carry out the production through separation of lysolecithin according to the present invention with use of hydrated lecithins such as hydrated gum-like material and paste-like lecithin admixed with water showing increased contents of impurities.

In another embodiment of the process for manufacturing vegetable lysolecithins according to the present invention, there is adopted an operational procedure which comprises subjecting the resultant lysolecithin product obtained after the above-mentioned, repeated extraction to an extraction with an alcohol to separate out a faction composed mainly of lysophosphatidylcholine from the alcohol-soluble portion and to obtain a fraction containing lysophosphatidylethanolamine as well as lyso-phosphatidylinositol and lysophosphatydic acid from the alcohol-insoluble portion, and this permits advantageous fractionation into various lyso-derivatives from the lysolecithin product obtained in the form of a mixture of lysoderivatives of phospholipids.

DETAILED DESCRIPTION OF THE PREFERRED EMBODIMENT

Referring particularly to hydrated lecithins used as a starting material in the operational procedure according to the present invention, any substances may be usable, only if they are hydrated products of lecithins or mixtures of phospholipids. And generally in the present invention, there can advantageously be utilized hydrated gum-like materials generated in the ordinary degumming step (raw vegetable oil → filtration → water treatment → separation of gum-like material) for vegetable oils, while normal, commercially available paste-formed lecithins produced by heating and concentrating such hydrated gum-like material, only after being treated with added water, can also advantageously used as a hydrated lecithin in the present invention, because of facilitated availability of such commercialized paste-formed lecithins. Yet, the hydrated gum-like material as mentioned in the first place is recommended to be used in an attempt to simplify the production steps as well as to suppress as far as possible the discoloration and flavor deterioration owing to heating. It is added that such hydrated lecithins generally show a water content in the range of 30 to 70 weight %.

Although such hydrated lecithins are obtainable from a variety of vegetable oils, the desired hydrated lecithin normally can be favorably produced from soybean oil which is easily available in terms of huge production volume. Needless to say, there can also be utilized other raw vegetable oils, such as rapeseed oil and corn oil. In connection to this, mention is to be made that among these raw oils, high-oleic safflower oil, palm oil and palm kernel oil produce vegetable lecithins containing mainly oleic acid as a unsaturated fatty acid, which lecithins can offer the characteristic feature of much more improved anti-oxidant capability as compared with soybean lecithin having a high content of polyene fatty acids. Such oleic-acid rich vegetable lecithins, for which application has been left undeveloped, currently are not filtered in the stage of crude oil but subjected directly to water treatment, followed by degumming, resulting in production of hydrated lecithins or hydrated gum-like materials showing high contents of impurities. The present invention can make use of even such hydrated, less pure lecithins to give high-purity lysolecithin products.

The present invention allows phospholipase $A_1$ or $A_2$, a hydrolysis enzyme, to act on such hydrated lecithin and by use of the hydrolysis action of such enzyme, produces the desired lysolecithin from lecithin (a mixture of phospholipids), or specifically converts phosphatidylcholine, phosphatidylethanolamine, phosphatidylinositol and phosphatidic acid into the corresponding lyso-derivatives, whereby the added amount of the enzyme and reaction conditions for enzymatic production of lysolecithins may suitably be selected and set, depending upon the pH value of hydrated lecithin and their solutions, the type and purity of such enzyme, etc. The reaction for enzymatic production of lysolecithins can be carried out, for example, by warming hydrated lecithin with a water content in the range of 30 to 70 weight %, without adjustment of its pH, at a temperature in the region of 30 to 60° C., preferably in the region of 50 to 55° C., and adding ordinarily a specified enzyme in a proportion of 0.03 to 0.1 weight % against the quantity of lecithin (a mixture of phospholipids), followed by continuous stirring for a period of time in the range of 12 to 60 hours, preferably in the range of 24 to 50 hours.

Such lysolecithin production reaction by means of enzymatic action is allowed to proceed until it is confirmed by thin-layer chromatography, etc. that the decomposition ratio of phosphatidyl choline, one of the major components of raw lecithin, reaches 60% or more, preferably 80% or more (which corresponds to an acid value of the reaction product in the range of 60 to 62). After the decomposition ratio of phosphatidyl choline is confirmed to be at 60% or more, preferably 80% or more, the resultant lysolecithin solution is admixed with an aqueous alkali solution, such as an aqueous sodium hydroxide solution, to adjust its acid value generally to less than 50, preferably less than 45, and if necessary, is subjected to a deactivation treatment by heating generally at 80 to 100° C. for 20 to 50 min., preferably at 85 to 95° C. for ca. 30 min. It is to be added that the addition of an alkali solution as mentioned in the above inhibits the acidification of the lysolecithin solution with fatty acids generated from enzymatic decomposition of lecithin (neutralization), and is intended to inhibit the breakdown or degradation of lysophospholipids. Since enzymes used show varied optimal pH values, it may advantageously be employable to control or regulate the enzymatic reaction while the reaction is under progress by adding an acidic or alkaline solution, various buffers, etc.

The above-mentioned deactivation treatment can inhibit effectively the action of the enzyme in the lysolecithin solution, whereas the present invention, in which the subsequent acetone treatment removes effectively the used enzyme, can advantageously eliminate the enzyme-deactivation step. Since the used enzyme (Phospholipase $A_1$ or $A_2$) is water-soluble, in short, the present invention permits a major portion of water to be removed by the separatory procedure for the lysolecithin phase with the firstly formulated acetone and can then allow the remaining water to immigrate into acetone during the subsequently repeated extraction procedure, thus resulting in simultaneous removal of the enzyme to give the high-purity lysolecithin product being entirely free from the enzyme.

In order to confirm how effectively the enzyme is removed by such procedure, an aqueous solution of the enzymatically decomposed lysolecithin obtained by hydrolysis of hydrated lecithin with the specified enzyme, or in other words the lysolecithin solution, was treated with acetone directly without being subjected to a deactivation treatment by heating, and the resultant powdered, high-purity lysolecithin product was admixed with the powdered, high-purity lecithin yielded by acetone treatment of ordinary lecithin not having undergone the enzyme treatment at a ratio of 1:1; the mixture was treated with water added and warmed at 50 to 55° C. for 24 hours, followed by determination of the remaining quantity of phosphatidyl choline by thin-layer chromatography, leading to the finding that the whole quantity of phosphatidyl choline originated from the added high-purity lecithin was retained as such. From this finding, it becomes evident that the acetone treatment in the present invention can perform effective removal of the enzyme from the lysolecithin product, and this suggests that elimination of such enzyme deactivation treatment step will contribute greatly to remarkable suppression of discoloration and flavor deterioration of the resultant lysolecithin.

In the present invention, furthermore, the lysolecithin solution as obtained by the enzymatic decomposition of hydrated lecithin with the above specified hydrolysis enzyme is formulated with acetone in a propitiation on a volume basis of 1 to 4, or 5 or more, against the water contained therein to thereby allow the lecithin portion to accumulate on the surface layer or in bottom layer and to be separated out from the water-phase portion. Namely, the present inventors after their intensive investigation discovered that despite the fact that lysolecithin becomes much more hydrophilic than lecithin after conversion to the lyso derivative, the aqueous solution of lysolecithin produced by the enzymatic degradation (or the lysolecithin solution) can allow the lysolecithin phase to float on the surface, making clear division from the lower water phase, and to precipitate on the bottom, making clear division from the upper water phase, by addition of acetone in the proportion on a volume basis of 1 to 4, and 5 or more, against the water contained therein, respectively.

In contrast to the above, such aqueous lysolecithin solution obtained by the enzymatic decomposition, when admixed with acetone in the proportion on a volume basis of less than 1 against the water contained therein, does not cause phase separation and when admixed with acetone in proportions on a volume basis of 4 to 5, produces vaguely defined three layers, out of which the upper layer immigrates partly to the intermediate and lower layers according as a length of time elapses, thus making the layer divisions unclear; this makes it impossible to collect the lysolecithin phase efficiently and therefore to separate out the same in increased yields. In connection to this, only the lower layer or upper layer was separated out from the three layers and treated with acetone, and then there was separated out lysolecithin in yields of 30 to 50% individually from the lower and upper layers, leading to the confirmation that when the above-mentioned three-layer division prevailed, lysolecithin was dispersed in such layers but did not exist as localized in one particular layer.

Acetone, which is to be formulated to such lysolecithin solution produced after enzymatic treatment to allow floatation or precipitation of the lysolecithin phase, is preferably distilled acetone as normally employed or may be any water-containing or hydrated acetone. In the present invention, the volume of acetone formulated to hydrated lysolecithin is calculated and specified against the total water content, and in cases when hydrated acetone is used, consequently, it is needless to say that the volume of acetone in hydrated acetone is required to be determined on the basis of the total water content produced by addition of the water content of the hydrated lysolecithin to the one in hydrated acetone.

In the present invention, this is then followed by repeated acetone extraction of the lysolecithin phase being separated out from the lysolecithin solution with the specified volume of acetone added to thereby remove through separation free fatty acids by-produced in the lysolecithin production reaction, oil-soluble impurities (oils) originated from the starting material, etc. as well as the remaining water simultaneously, resulting in production of high-purity lysolecithin product (a mixture of phospholipids including lysolecithins) in the form of powder. The acetone treatment of the lysolecithin phase can be carried out in the same manner as the conventional extraction treatment with use of acetone, and the added volume of acetone or a number of repeated treatments are to be suitably determined so that dehydration or water removal and defatting may be effected completely, whereby since the acetone treatment of separated lysolecithin phase is intended to serve the double purpose to achieve not only defatting but also dehydration, it is desirable to conduct the above acetone extraction treatment using normally equal to or more, preferably 3 to 5 times, the volume of the lysolecithin phase. In light of the fact that lysolecithin shows stronger water-absorbing capacity than the starting lecithin, it is recommendable to use distilled acetone free from moisture in order to effect effective dehydration.

Generally, the powdered lysolecithin product as obtained by the acetone extraction treatment shows a high degree of purity, but in cases where there is used the oleic-acid rich, vegetable lecithin which, as described in the above, is produced by hydration treatment and degumming of crude oil without being filtered, the resultant hydrated lecithin contains impurities being unable to be removed after the acetone extraction treatment; in the present invention, accordingly, there may advantageously be employed a procedure which involves subjecting the lysolecithin product obtained from the hydrated lecithin containing such impurities to an extraction treatment with a specified non-polar organic solvent being exemplified by saturated hydrocarbons having 5 to 8 carbon atoms, such as pentane, hexane, heptane and octane, to thereby give the high-purity lysolecithin product by removal through elution of such impurities, while addition of various buffer solutions on the occasion of enzymatic reaction treatment permits constituent salts to be removed effectively, as well.

In view of the fact that the lysolecithin product from the lysolecithin phase through acetone extraction is yielded in the form of a mixture consisting of the phospholipids converted or not converted into their lyso-derivatives and the phospholipids not converted into their lyso-derivatives with phospholipase $A_1$ or $A_2$ which individually correspond to a mixture of the phospholipids constituting raw lecithin, according to the present invention, there may advantageously adopted a procedure which involves furthermore subjecting such lysolecithin product to an extraction treatment with a $C_1$–$C_3$ alcohol, such as methanol, ethanol, propanol and isopropanol, or an aqueous alcohol consisting of 1 to 10 weight % of water contained in such an alcohol to separate a fraction composed mainly of lysophosphatidylcholine and a fraction containing lysophosphatidylethanolaimne, lysophosphatidylinositol and lysophosphatidic acid from the resultant alcohol-soluble and alcohol-insoluble portions, respectively, thus enabling the lyso-derivative of each phospholipid constituent to be separated out advantageously.

In the process for manufacturing vegetable lysolecithins according to the present invention, a variety of the known separatory procedures, such as the conventional settling method and centrifugation method, can suitably be employed in order to conduct solid-liquid separation in the separation of the lysolecithin phase accumulated in the surface or bottom layer through formulation of the lysolecithin solution with the specified volume of acetone, as well as acetone extraction treatment of the separated lysolecithin phase, extraction treatment with an alcohol or aqueous alcohol and extraction treatment with a non-polar organic solvent.

As is evident from the above description and will be apparent after a review of the following detailed description of the disclosed embodiments, the present invention is intended to produce vegetable lysolecithins in the form of powder from hydrated vegetable lecithins used as a starting material by allowing phospholipase $A_1$ or $A_2$ to act on the hydrated lecithin to modify the lecithin into a lysolecithin, then adding a specified volume of acetone to the resultant aqueous solution containing the lysolecithin to thereby either float or precipitate the lysolecithin phase, then separating out said lysolecithin phase, followed by repetition of the acetone extraction, wherein this invention provides the major technological significance in that the said lysolecithin product exhibits markedly reduced degree of discoloration as well as extremely improved flavor in terms of smell, taste, etc. and can consequently find a widened range of application not only in the food processing industry but also the pharmaceutical industry and their related fields.

The manufacturing process according to the present invention, as compared with the conventional counterparts, does neither decrease the production yields of lysolecithin products nor bring about increases in production costs, and all the more, the process makes it feasible to eliminate the concentration/drying, enzyme deactivation and filtration steps, thus permitting the investment cost on the production facilities to be curtailed and also offering the potential advantage of increasing production cycles.

Furthermore, the manufacturing process of this invention can produce high-purity lysolecithin products and fractionated products, using as a starting material hydrated lecithins with an increased content of impurities being produced from vegetable crude oils without filtration, and therefore enables the desired lysolecithin products to be manufactured from unused lecithins, especially high-oleic lecithins, while as a result, it can yield lysolecithin products with improved oxidation resistance, as well, thus opening up a way for diversified utilization of lecithin.

Below described are several examples of the present invention to illustrate the present invention more particularly, but needless to say, the present invention is in no way limited by the description of such examples. Furthermore, it is to be understood that various changes, modification, improvements, etc. can be made to the present invention on the basis of the knowledge of a man of ordinary skill in the art without departing from the spirit and scope of the present invention.

In the below-described examples, the percentages are intended to designate those on a weight basis, and the used acetone means distilled acetone, while the following symbols are used to stand for phospholipids and their lyso-derivatives, respectively: PC: phosphatidylcholine, PE: phosphatidylethanolamine, PI: phosphatidylinositol, PA: phosphatidic acid, LPC: lysophosphatidylcholine, LPE: lysophosphatidylethanolamine, and LPA: lysophosphatidic acid.

EXAMPLE 1

A 1.2 kg quantity of hydrated lecithin with a water content of 50% (a mixture of phospholipids), or a hydrated gum-like material obtained in the degumming step for soybean oil, was warmed at 50 to 55° C. and admixed under stirring with 0.2 ml of Lecitase 10 L (produced by Novo Nordisk Co. of Japan, 11000 units/ml), a hydrolysis enzyme of Phospholipase $A_2$. to conduct an enzymatic reaction for 24 hours, and the reaction solution was admixed with 40 ml of 5N aqueous sodium hydroxide solution at the point of time when the reaction product showed an acid value of 60 as determined by the procedure set forth in "Standard Methods for the Analysis of Fats, Oils and Related Materials", Section 4.2.1. - 1996 edition, "Acid Value", edited by The Japan Oil Chemists' Society, to thereby adjust the acid value to below 45, and heated to raise the temperature to 85 to 90° C., followed by maintaining at the same temperature for 30 min. to conduct deactivation of the enzyme, thus giving the objective aqueous lysolecithin solution, which was then admixed with water to make the total to 1.2 kg in quantity.

300 g of the aqueous lysolecithin solution obtained by the above procedure was admixed with 300 ml of acetone (which corresponded to about twice the volume of the water contained in the aqueous lysolecithin solution) and the solution mixture was stirred to allow the lysolecithin phase to float on the surface, resulting in splitting from the water phase. The upper layer of the lysolecithin phase was separated out by removing the lower layer of the water phase, and extracted five times with each 700 ml portion of acetone to remove through elution free fatty acids (by-produced in the lysolecithin production reaction) contained in such lysolecithin phase, oil components such as neutral oils and sterols originated from the starting material and the remaining water, and the lysolecithin phase obtained after such acetone extraction treatment was freed of the remaining acetone under reduced pressure to give 64 g of the high-purity lysolecithin product in the form of powder.

EXAMPLE 2

A 300 g quantity of the aqueous lysolecithin solution obtained in Example 1 was admixed with 900 ml of acetone (which corresponded to about six times the volume of the water contained in the aqueous lysolecithin solution) and the solution mixture was stirred to allow the lysolecithin phase to precipitate.

The lysolecithin phase was separated out by removing the water phase (the upper layer) over the precipitated lysolecithin phase and extracted five times with each 700 ml portion of acetone to remove fatty acids, oil components and remaining water, etc., and the lysolecithin phase produced after the acetone extraction was freed of the remaining acetone under reduced pressure to give 62.7 g of the high-quality lysolecithin product in the form of powder.

Comparative Example 1

A 300 g quantity of the aqueous lysolecithin solution as obtained in Example 1 described above was dried under reduced pressure to convert to a paste-formed lysolecithin, which was then admixed with 1% of Celite (filtering aid) and filtered through filter paper with warming and under reduced pressure to give 145 g of a paste-formed lysolecithin product. The paste-formed lysolecithin product was extracted five times with each 700 ml portion of acetone, and the lysolecithin phase produced after the acetone extraction was freed of the remaining acetone under reduced pressure to give 66.7 g of the high-quality lysolecithin product in the form of powder.

Comparative Example 2

A 300 g quantity of the aqueous lysolecithin solution obtained in Example 1 described above was admixed with 675 ml of acetone (which corresponded to 4.5 times the volume of the water contained in the aqueous lysolecithin solution) and the solution mixture was stirred to split into three layers, or the upper, intermediate and lower layers. Because the split upper layer immigrated little by little into the lower layer to make the boundary indefinite, the upper layer was separated out immediately after splitting and then extracted five times with each 700 ml portion of acetone, and the resultant lysolecithin phase was freed of the remaining acetone under reduced pressure to give 30.5 g of the high-quality lysolecithin product in the form of powder.

Evaluation

30 The different high-quality lysolecithin products in the form of powder as obtained in the above Examples 1 and 2 and Comparative Examples 1 and 2 were investigated for acetone soluble content, major phospholipid constituent and discoloration degree in accordance with the testing methods set forth in "Standard Methods for the Analysis of Fats, Oils and Related Materials" - 1996 edition, edited by the "Japan Oil Chemists' Society", with the results being tabulated below in Table 1 together with the yields expressed as produced quantity and percentage, whereby the acetone soluble denotes a measure for the degree of purity each of the lysolecithin products; the smaller the magnitude of value, the higher the degree of purity.

TABLE 1

|  | Examples | | Comparative Examples | |
| --- | --- | --- | --- | --- |
|  | 1 | 2 | 1 | 2 |
| Yield, g | 64 | 62.7 | 66.7 | 30.5 |
| Yield*, % | 96 | 94 | 100 | 45.7 |
| Acetone soluble, % | 2.68 | 2.56 | 2.61 | 2.64 |
| Phospholipid composition, % | | | | |
| PC | 6.5 | 6.0 | 6.2 | 6.8 |
| PE | 3.9 | 4.0 | 3.7 | 3.0 |
| PI | 11.0 | 11.5 | 11.3 | 10.8 |
| PA | 2.0 | 2.5 | 2.3 | 1.9 |
| LPC | 22.5 | 23.9 | 23.0 | 22.4 |
| LPE | 8.0 | 7.8 | 8.5 | 9.0 |
| LPA | 7.5 | 6.7 | 7.1 | 7.5 |
| Discoloration*[2] | 50Y + 11R | 50Y + 12R | 60Y + 21R | 50Y + 11R |

Notes:
*[1] Among the major phospholipid constituents, PC, PE, PI and PA, PI does not undergo enzymatic degradation with phospholipase $A_2$, whereas the other phospholipid constituents (PC, PE and PA) are degraded to their individual lyso derivatives, and because the differences in rates of degradation among them make it difficult to determine the theoretical yields, the yields in terms of percentage are expressed as a relative value based on the yield in Comparative Example 1 taken as 100%.
*[2] In accordance with the procedure set forth in "Standard Methods for the Analysis of Fats, Oils and Related Materials", 2.2.1.1-1996, Section "Color (The Lovibond Method)", 10 g of a sample was dissolved in 50 ml of benzene and the solution was measured for color by means of a Lovibond colorimeter with use of a 1-inch cell.

As is evident from the results shown in Table 1, Examples 1 and 2 in which the procedure of the present invention was conducted gave 94 to 96% in relative yield as compared with Comparative Example 1 in which the conventional filtration method was employed, and was observed to achieve higher yields than Comparative Example 2. Referring to the acetone soluble and phospholipid composition which designate the degree of purity of lysolecithin, there is observed almost no difference between Examples 1 and 2 and Comparative Example 1, whereas the red value (R), an index of the degree of discoloration, was found to be increased as high as 21 in Comparative Example 1 but to be lowered as small as 11 to 12 in Examples 1 and 2, leading to the observation that a remarkable difference existed in degree of discoloration among the resultant phospholipids. The lysolecithin products obtained in Examples 1 and 2 excelled by far in terms of smell the one produced in Comparative Example 1 by following the conventional filtration method, and from the conventionally known empirical conclusion that runs "lowered degree of discoloration offers improved flavor", it becomes evident that the lysolecithin products obtained in Examples 1 and 2, with their lowered degree of discoloration as mentioned in the above, also excel in terms of flavor.

EXAMPLE 3

A 1 kg quantity of hydrated soybean lecithin with a water content of 60% was warmed at 50 to 55° C. and then admixed with 0.15 ml of Lecitase 10 L as a phospholipase $A_2$ (hydrolysis enzyme), under stirring, to conduct an enzymatic reaction for 24 hours, and the reaction solution was admixed with 26 ml of 5N aqueous sodium hydroxide solution at the point of time when it showed an acid value of 60 to thereby adjust the acid value to below 45, and furthermore admixed with 1.2 liters (which corresponded to twice the volume of the water content of the enzymatic reaction solution) of acetone, directly without being subjected to the enzyme deactivation step, followed by stirring to allow the lysolecithin phase to float on the surface and five times extraction of the lysolecithin phase with a 3 liters portion of acetone each after removal of the lower water phase. The lysolecithin phase after acetone extraction treatment was freed of the remaining acetone under reduced pressure to give 175 g (yield: 43.8% against the starting soybean lecithin) of the high-purity lysolecithin product in the form of powder, which lysolecithin product is to be referred to as "Powder A".

On the other hand, 1 kg of hydrated soybean lecithin with a water content of 40% was warmed at 50 to 55° C. and then admixed with a solution of 30 mg of phospholipase $A_1$ (produced by Sankyo Co. of Japan; 155 units/mg) as a hydrolysis enzyme in a small amount of water, under stirring, to conduct an enzymatic reaction for 48 hours, and the reaction solution was admixed with 30 ml of 5N aqueous sodium hydroxide solution at the point of time when it showed an acid value of 60 to thereby adjust the acid value to below 45, and furthermore with 2.4 liters (which corresponded to six times the volume of the water content of the enzymatic reaction solution) of acetone, directly without being subjected to the enzyme deactivation step, followed by stirring to allow the lysolecithin phase to precipitate on the bottom and six times extraction of the lysolecithin phase with a 3 liters portion of acetone each after removal of the upper water phase. The lysolecithin phase after acetone extraction treatment was freed of the remaining acetone under reduced pressure to give 245 g (yield: 40.8% against the starting soybean lecithin) of the high-purity lysolecithin product in the form of powder, which lysolecithin product is to be referred to as "Powder B".

The Powders A and B obtained in the above two experiments were measured for a degree of discoloration by the previously mentioned Lovibond method, with the result that both of the red values (R) were in the range of 6 to 7, which demonstrated a marked difference in degree of discoloration from the red values of 11 to 12 in Examples 1 and 2 (refer to Table 1) and also their greater excellence in flavor. This is considered to owing to elimination of the heating step for the enzyme inactivation.

Also, 10 g each of the above Powders A and B were mixed with 10 g of high-purity, powder-formed soybean lecithin (obtained by treating ordinary paste-formed soybean lecithin with acetone), respectively, followed by addition of 50 ml of water to be converted into a solution form, and after the resultant solutions were warmed at 50 to 55° C. and maintained at the same temperature for 50 hours under stirring, the solutions were investigated for their individual phospholipid compositions, with the results being tabulated bellow in Table 2 together with the composition prior to warming:

TABLE 2

| Phospholipid composition, % | Mixed product of Powder A Warming | | Mixed product of Powder B Warming | |
|---|---|---|---|---|
| | Before | After | Before | After |
| PC | 16.9 | 15.5 | 16.7 | 15.6 |
| PE | 12.9 | 11.2 | 11.8 | 10.2 |
| PI | 13.3 | 12.1 | 9.3 | 9.1 |
| PA | 5.9 | 4.8 | 7.1 | 6.0 |

As is evident from the above Table, both of the mixed products of Powders A and B showed a slightly lowered content of each phospholipid after heating, and from the PI analytical values in the mixed product of Powder A, it is assumed that such changes were owing to degradation of phospholipids caused by heating over a prolonged period of time; namely, the value of PI was in practice found to be slightly lower after heating, as well, although it is theoretically considered to be maintained, since phospholipase $A_2$ (Lecitase 10 L) fails to enzymatically degrade PI. In any way, both mixed products were not observed to exhibit a radical drop in each phospholipid content by the remaining enzyme, and consequently, this indicates that the acetone treatment according to the present invention constitutes the effective enzyme-removal means, when taking into consideration the water solubility of used enzymes (phospholipase $A_1$ and $A_2$).

EXAMPLE 4

A 1 kg quantity of hydrated safflower lecithin with a water content of 70% produced from crude oil not being subjected to filtration was warmed at 50 to 55° C. and then admixed with 0.12 ml of Lecitase 10 L mentioned in the above as a hydrolysis enzyme, under stirring, to conduct an enzymatic reaction for 24 hours, and the reaction solution was admixed with 25 ml of 5N aqueous sodium hydroxide solution at the point of time when it showed an acid value of 60 to thereby adjust the acid value to below 45, yielding the objective lysolecithin solution.

Then, the resultant lysolecithin solution was admixed with 4.2 liters (which corresponded to about six times the volume of the water content of the lysolecithin solution) of acetone, directly without being subjected to the enzyme deactivation step, followed by stirring to allow the lysolecithin phase to precipitate on the bottom and six times extraction of the lysolecithin phase with a 3 liters portion of acetone each after removal of the upper water phase. Thereafter, the lysolecithin phase after acetone extraction treatment was freed of the remaining acetone under reduced pressure to give 130 g of the lysolecithin product in the form of powder. However, the lysolecithin product showed a toluene insoluble content of 2.5%, leading to the observation that it contained impurities other than phospholipids being owing to elimination of the crude-oil filtration step, and the product as such is out of the specification that sets forth less than 0.5% of toluene insoluble content and cannot therefore be commercialized.

Under these circumstances, 40 g of the above lysolecithin product in the form of powder was dissolved in 200 ml of n-hexane, and after the solution was filtered through filter paper and then freed of hexane under reduced pressure, the resultant purified lysolecithin product in quantity of 38.5 g, with its toluene insoluble content of 0.08%, was found to be provided with an enhanced degree of purity enough to meet the abovementioned specification.

Also, 40 g of the above off-specification lysolecithin product in the form of powder was extracted three times with each 120 ml portion of ethanol, and only the supernatant ethanol phases were collected and freed of ethanol under reduced pressure to give a fraction composed mainly of LPC (8 g; an LPC content of 62%). The fraction showed a toluene insoluble content of 0.1%, and it can be concluded that when the ethanol extraction is carried out, the high-purity fraction can be produced by collection of the supernatant extract phases, followed by removal of the solvent (ethanol).

Furthermore, 60 g of the high-purity lysolecithin obtained in the above by extraction with n-hexane was extracted three times with each 200 ml portion of ethanol to be divided into the ethanol-soluble and ethanol-insoluble parts. The ethanol-soluble part was concentrated to dryness to give 11 g of a fraction composed mainly of LPC (an LPC content of 65%), while the ethanol-insoluble part was dried to give 45 g of a fraction containing LPE, LPA, etc.

As is described in the above, even hydrated lecithins produced without filtration of crude oil, such as hydrated gum-like materials with increased contents of impurities, can be used as a starting material to produce high-purity lysolecithin products or lysolecithin fractionated products, merely by subjecting them to the consecutive enzyme and acetone treatments, followed by the extraction treatment with such a non-polar organic solvent as n-hexane or such a polar organic solvent as ethanol or combined treatments thereof.

What is claimed:

1. A process for manufacturing a vegetable lysolecithin from a hydrated lecithin used as a starting material, which comprises allowing a hydrolysis enzyme consisting of phospholipase $A_1$ or $A_2$ to act on the hydrated lecithin to produce a lysolecithin, then adding under stirring to the resultant lysolecithin solution acetone in a proportion on a volume basis of either (i) 1 to 4, or (ii) at least 5 against the water contained in said resultant lysolecithin solution to thereby either float or precipitate the lysolecithin phase, and separating out said lysolecithin phase, followed by repetition of the acetone extraction procedure to produce a vegetable lysolecithin with a high degree of purity by separating for removal free fatty acids by-produced in the said lysolecithin production reaction as well as oil-soluble impurities originated from the starting material.

2. A process for manufacturing a vegetable lysolecithin as claimed in claim 1, wherein said hydrated lecithin is a hydrated gum-like material produced in the degumming step for vegetable oils.

3. A process for manufacturing a vegetable lysolecithin as claimed in claim 1, wherein said hydrated lecithin is a water-treated, paste-formed lecithin.

4. A process for manufacturing a vegetable lysolecithin as claimed in claim 1, wherein said enzymatic reaction is carried out after admixing said hydrated lecithin with an aqueous alkaline solution, aqueous acidic solution or buffer to secure the optimal pH value for said enzyme.

5. A process for manufacturing a vegetable lysolecithin as claimed in claim 1, wherein the resultant lysolecithin solution is subjected to a deactivation reaction after production of said lysolecithin but prior to treatment with added acetone.

6. A process for manufacturing a vegetable lysolecithin as claimed in claim 1, wherein after production of said lysolecithin, the resultant lysolecithin solution is subjected to treatment with added acetone directly without undergoing the deactivation reaction.

7. A process for manufacturing a vegetable lysolecithin as claimed in claim 1, wherein after the said repeated acetone extraction, the resultant lysolecithin product is subjected to an extraction treatment with a non-polar organic solvent to thereby produce a lysolecithin product with an enhanced degree of purity.

8. A process for manufacturing a vegetable lysolecithin as claimed in claim 1, wherein after the said repeated acetone extraction, the resultant lysolecithin product is extracted with an alcohol or aqueous alcohol to obtain a fraction composed mainly of lysophosphatidylcholine from the alcohol-soluble portion and simultaneously to obtain a fraction containing lysophosphatidylethanolamine and lysophosphatidylinositol as well as lysophosphatidic acid from the alcohol-insoluble portion.

* * * * *